United States Patent
Itagaki

(10) Patent No.: US 7,612,236 B2
(45) Date of Patent: Nov. 3, 2009

(54) METHOD FOR PRODUCING OPTICALLY ACTIVE BISAMIDOALCOHOL COMPOUND

(75) Inventor: Makoto Itagaki, Katano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 521 days.

(21) Appl. No.: 10/580,691

(22) PCT Filed: Dec. 21, 2004

(86) PCT No.: PCT/JP2004/019668

§ 371 (c)(1), (2), (4) Date: May 26, 2006

(87) PCT Pub. No.: WO2005/061435

PCT Pub. Date: Jul. 7, 2005

(65) Prior Publication Data

US 2007/0100163 A1 May 3, 2007

(30) Foreign Application Priority Data

Dec. 22, 2003 (JP) ............................. 2003-424579

(51) Int. Cl.
*C07C 231/02* (2006.01)
*C07C 233/05* (2006.01)

(52) U.S. Cl. .................... 564/139; 564/135; 564/158; 564/160

(58) Field of Classification Search ................ 564/135, 564/139, 158, 160
See application file for complete search history.

(56) References Cited

FOREIGN PATENT DOCUMENTS

| EP | 0 895 992 A2 | 2/1999 |
|---|---|---|
| JP | 5-221935 A | 8/1993 |
| JP | 6-199747 A | 7/1994 |
| JP | 8-109158 A | 4/1996 |
| JP | 9-255668 A | 9/1997 |
| JP | 11-171874 | 6/1999 |

OTHER PUBLICATIONS

Weissberg et a, Synlett, 2002, No. 2, pp. 247-250.*
Brown et al, Synthetic Communications, 1988, vol. 18, No. 15, pp. 1801-1806.*
S.E. Denmark, et al. "Cyclopropanation with Diazomethane and Bis(Oxazoline) Palladium (II) Complexes, Journal of Organic Chemistry, American Chemical Society, vol. 62, No. 10, May 16, 1997, pp. 337-3389.
D. Muller et al., "21. $C_2$-Symmetric 4,4',5,5'-Tetrahydrobi(oxazoles) and 4,4'5,5'-Tetrahydro-2,2'-methylenebis[oxazoles] as Chiral Ligands for Enantioselective Catalysis", Helvetica Chimica Acta—vol. 74, 1991, pp. 232-241.
D. Evans et al., "An Improved Procedure for the Preparation of 2,2-Bis[2-[4(S)-*tert*-butyl-1,3-oxazolinyl]] propane [(S,S)-*tert*-Butylbis(oxazoline)] and Derived Cooper (II) Complexes", J. Org. Chem., 1998, 63, pp. 4541-4544.

* cited by examiner

Primary Examiner—Shailendra Kumar
(74) Attorney, Agent, or Firm—Sughrue Mion, PLLC

(57) ABSTRACT

It is provided that a method for producing an optically active bisamidoalcohol compound represented by the formula (3):

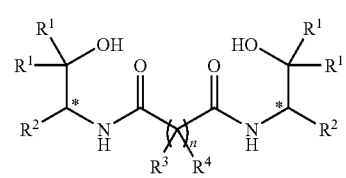

(3)

wherein $R^1$ represents a C1-6 alkyl group, an optionally substituted phenyl group, an optionally substituted aralkyl group or a hydrogen atom, or two $R^1$s, which are bonded to the same carbon atom, are bonded to form a ring together with the carbon atom to which they are bonded,
$R^2$ represents a C1-6 alkyl group, an optionally substituted phenyl group, a 1-naphthyl group, a 2-naphthyl group or an optionally substituted aralkyl group,
$R^3$ and $R^4$ are the same or different, and each represents a hydrogen atom or C1-3 alkyl group,
m represents an integer of 0 to 2, and
* represents an asymmetric center,
which comprises reacting an optically active aminoalcohol compound represented by the formula (1):

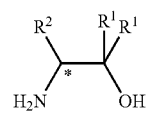

(1)

wherein $R^1$, $R^2$ and * are as defined above,
with a diester compound represented by the formula (2):

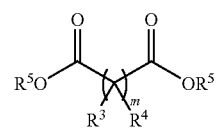

(2)

wherein $R^3$, $R^4$ and m are as defined above and $R^5$ represents a C1-3 alkyl group,
in the presence of a lithium compound.

7 Claims, No Drawings

METHOD FOR PRODUCING OPTICALLY ACTIVE BISAMIDOALCOHOL COMPOUND

This application is a 371 of PCT/JP04/19668, filed Dec. 21, 2004.

TECHNICAL FIELD

The present invention relates to a method for producing an optically active bisamidoalcohol compound which is used as an intermediate for an optically active bisoxazoline compound which is a ligand of an asymmetric synthesis catalyst.

BACKGROUND ART

As a method for producing an optically active bisamidoalcohol compound which is used as an intermediate for an optically active bisoxazoline compound which is a ligand of an asymmetric synthesis catalyst (e.g. Patent document 1 and 2), for example, a method for mixing an optically active aminoalcohol and dimethyl malonate in the absence of a solvent and heating thereof (e.g. Non-patent document 1) and a method for synthesizing by reacting an optically active aminoalcohol with a malonyl dichloride compound in the presence of a base have been known.

Patent document 1: JP 11-171874 A
Patent document 2: JP 2000-80060 A
Non-patent document 1: Helvetica Chimica Acta, 74, 232 (1991)
Non-patent document 2: J. Org. Chem., 63, 4541(1998)

DISCLOSURE OF THE INVENTION

According to the present invention, an optically active bisamidoalcohol compound can be efficiently manufactured without a step of acid chlorination.

The first embodiment of the present invention relates to a method for producing an optically active bisamidoalcohol compound represented by the formula (3):

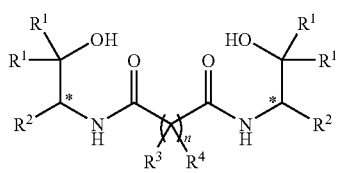

wherein $R^1$ represents a C1-6 alkyl group, an optionally substituted phenyl group, an optionally substituted aralkyl group or a hydrogen atom, or two $R^1$s, which are bonded to the same carbon atom, are bonded to form a ring together with the carbon atom to which they are bonded, $R^2$ represents a C1-6 alkyl group, an optionally substituted phenyl group, a 1-naphthyl group, a 2-naphthyl group or an optionally substituted aralkyl group, $R^3$ and $R^4$ are the same or different, and each represents a hydrogen atom or C1-3 alkyl group, m represents an integer of 0 to 2, and \* represents an asymmetric center, which comprises reacting an optically active aminoalcohol compound represented by the formula (1):

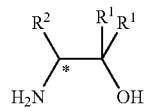

wherein $R^1$, $R^2$ and \* are as defined above, with a diester compound represented by the formula (2):

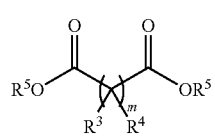

wherein $R^3$, $R^4$ and m are as defined above and $R^5$ represents a C1-3 alkyl group, in the presence of a lithium compound.

BEST MODE FOR CARRYING OUT THE PRESENT INVENTION

The present invention will be illustrated in detail below.

A substituent of the optically active aminoalcohol compound represented by the formula (1) (hereinafter, simply referred to as the optically active aminoalcohol compound (1)) will be illustrated below.

Examples of the C1-6 alkyl groups represented by $R^1$ or $R^2$ include straight or branched chain C1-6 alkyl groups such as a methyl, ethyl, n-propyl, isopropyl, n-butyl, isobutyl, tert-butyl, n-pentyl and n-hexyl group.

Examples of the optionally substituted phenyl groups represented by $R^1$ or $R^2$ include phenyl groups which may be substituted with at least one selected from a C1-6 alkyl group and a C1-6 alkoxy group such as an unsubstituted phenyl group; phenyl groups substituted with a C1-6 alkyl group like the above such as a 3-methylphenyl and 4-methylphenyl group; and phenyl groups substituted with a C1-6 alkoxy group (e.g. a methoxy, ethoxy, propoxy, butoxy, pentyloxy, and hexyloxy group) such as a 2-methoxyphenyl and 4-methoxyphenyl group.

Examples of the optionally substituted aralkyl groups represented by $R^1$ or $R^2$ include optionally substituted C7-16 aralkyl groups (in more detail, for example, C1-6 alkyl groups substituted with a naphthyl group or an optionally substituted phenyl group). As the substituents of the optionally substituted C7-16 aralkyl groups, at least one substituent selected from a C1-6 alkyl group and a C1-6 alkoxy group is exemplified. Specific examples of the optionally substituted aralkyl groups include C1-6 alkyl groups substituted with a phenyl group which may be substituted with a C1-6 alkyl group or a C1-6 alkoxy group, and C1-6 alkyl groups substituted with a naphthyl group such as a benzyl, 4-methylbenzyl, 4-methoxybenzyl, 1-naphthylmethyl and 2-naphthylmethyl group.

As the ring formed by bonding two $R^1$s, which are bonded to the same carbon atom, together with the carbon atom to which they are bonded, C3-6 cycloalkanes such as a cyclopropane ring, a cyclobutane ring, a cyclopentane ring and a cyclohexane ring are exemplified.

Herein, Examples of the optically active aminoalcohol compound (1) include (R)-2-amino-propanol, (R)-2-amino-1,1-dimethylpropanol, (R)-2-amino-1,1-diethylpropanol, (R)-2-amino-1,1-di(n-propyl)propanol, (R)-2-amino-1,1-diphenylpropanol, (R)-2-amino-1,1-di(4-methylphenyl)propanol, (R)-2-amino-1,1-di(2-methoxyphenyl)propanol, (R)-2-amino-1,1-di(4-methoxyphenyl)propanol, (R)-2-amino-1,1-dibenzylpropanol, 1-((R)-1-aminoethyl)cyclobutanol, 1-((R)-1-aminoethyl)cyclopentanol, 1-((R)-1-aminoethyl)cyclohexanol, (R)-2-amino-3-methylbutanol, (R)-2-amino-3-methyl-1,1-dimethylbutanol, (R)-2-amino-3-methyl-1,1-diethylbutanol, (R)-2-amino-3-methyl-1,1-di(n-propyl)butanol, (R)-2-amino-3-methyl-1,1-diphenylbutanol, (R)-2-amino-3-methyl-1,1-di(4-methylphenyl)butanol, (R)-2-amino-3-methyl-1,1-di(2-methoxyphenyl)butanol, (R)-2-amino-3-methyl-1,1-di(4-methoxyphenyl)butanol, (R)-2-amino-3-methyl-1,1-dibenzylbutanol, 1-((R)-1-amino-2-methylpropyl)cyclobutanol, 1-((R)-1-amino-2-methylpropyl)cyclopentanol, 1-((R)-1-amino-2-methylpropyl)cyclohexanol, (R)-2-amino-4-methylpentanol, (R)-2-amino-4-methyl-1,1-dimethylpentanol, (R)-2-amino-4-methyl-1,1-diethylpentanol, (R)-2-amino-4-methyl-1,1-di(n-propyl)pentanol, (R)-2-amino-4-methyl-1,1-diphenylpentanol, (R)-2-amino-4-methyl-1,1-di(4-methylphenyl)pentanol, (R)-2-amino-4-methyl-1,1-di(2-methoxyphenyl)pentanol, (R)-2-amino-4-methyl-1,1-di(4-methoxyphenyl)pentanol, (R)-2-amino-4-methyl-1,1-dibenzylpentanol, 1-((R)-1-amino-3-methylbutyl)cyclobutanol, 1-((R)-1-amino-3-methylbutyl)cyclopentanol, 1-((R)-1-amino-3-methylbutyl)cyclohexanol, (R)-2-amino-3,3-dimethylbutanol, (R)-2-amino-3,3-dimethyl-1,1-dimethylbutanol, (R)-2-amino-3,3-dimethyl-1,1-diethylbutanol, (R)-2-amino-3,3-dimethyl-1,1-di(n-propyl)butanol, (R)-2-amino-3,3-dimethyl-1,1-diphenylbutanol, (R)-2-amino-3,3-dimethyl-1,1-di(4-methylphenyl)butanol, (R)-2-amino-3,3-dimethyl-1,1-di(2-methoxyphenyl)butanol, (R)-2-amino-3,3-dimethyl-1,1-di(4-methoxyphenyl)butanol, (R)-2-amino-3,3-dimethyl-1,1-dibenzylbutanol, 1-((R)-1-amino-2,2-dimethylpropyl)cyclobutanol, 1-((R)-1-amino-2,2-dimethylpropyl)cyclopentanol, 1-((R)-1-amino-2,2-dimethylpropyl)cyclohexanol, (R)-2-amino-2-phenylethanol, (R)-2-amino-2-phenyl-1,1-dimethylethanol, (R)-2-amino-2-phenyl-1,1-diethylethanol, (R)-2-amino-2-phenyl-1,1-di(n-propyl)ethanol, (R)-2-amino-2-phenyl-1,1-diphenylethanol, (R)-2-amino-2-phenyl-1,1-di(4-methylphenyl)ethanol, (R)-2-amino-2-phenyl-1,1-di(2-methoxyphenyl)ethanol, (R)-2-amino-2-phenyl-1,1-di(4-methoxyphenyl)ethanol, (R)-2-amino-2-phenyl-1,1-dibenzylethanol, 1-((R)-1-amino-1-phenylmethyl)cyclobutanol, 1-((R)-1-amino-1-phenylmethyl)cyclopentanol, 1-((R)-1-amino-1-phenylmethyl)cyclohexanol, (R)-2-amino-2-(1-naphthyl)ethanol, (R)-2-amino-2-(1-naphthyl)-1,1-dimethylethanol, (R)-2-amino-2-(1-naphthyl)-1,1-diethylethanol, (R)-2-amino-2-(1-naphthyl)-1,1-di-n-propylethanol, (R)-2-amino-2-(1-naphthyl)-1,1-diphenylethanol, (R)-2-amino-2-(1-naphthyl)-1,1-di-(4-methylphenyl)ethanol, (R)-2-amino-2-(1-naphthyl)-1,1-di-(2-methoxyphenyl)ethanol, (R)-2-amino-2-(1-naphthyl)-1,1-di-(4-methoxyphenyl)ethanol, (R)-2-amino-2-(1-naphthyl)-1,1-dibenzylethanol, 1-((R)-1-amino-1-(1-naphthyl)methyl)cyclobutanol, 1-((R)-1-amino-1-(1-naphthyl)methyl)cyclopentanol, 1-((R)-1-amino-1-(1-naphthyl)methyl)cyclohexanol, (R)-2-amino-2-(2-naphthyl)ethanol, (R)-2-amino-2-(2-naphthyl)-1,1-dimethylethanol, (R)-2-amino-2-(2-naphthyl)-1,1-diethylethanol, (R)-2-amino-2-(2-naphthyl)-1,1-di(n-propyl)ethanol, (R)-2-amino-2-(2-naphthyl)-1,1-diphenylethanol, (R)-2-amino-2-(2-naphthyl)-1,1-di(4-methylphenyl)ethanol, (R)-2-amino-2-(2-naphthyl)-1,1-di(2-methoxyphenyl)ethanol, (R)-2-amino-2-(2-naphthyl)-1,1-di(4-methoxyphenyl)ethanol, (R)-2-amino-2-(2-naphthyl)-1,1-dibenzylethanol, 1-((R)-1-amino-1-(2-naphthyl)methyl)cyclobutanol, 1-(R)-1-amino-1-(2-naphthyl)methyl)cyclopentanol, 1-(R)-1-amino-1-(2-naphthyl)methyl)cyclohexanol, (R)-2-amino-3-phenylpropanol, (R)-2-amino-3-phenyl-1,1-dimethylpropanol, (R)-2-amino-3-phenyl-1,1-diethylpropanol, (R)-2-amino-3-phenyl-1,1-di(n-propyl)propanol, (R)-2-amino-3-phenyl-1,1-diphenylpropanol, (R)-2-amino-3-phenyl-1,1-di(4-methylphenyl)propanol, (R)-2-amino-3-phenyl-1,1-di(2-methoxyphenyl)propanol, (R)-2-amino-3-phenyl-1,1-di(4-methoxyphenyl)propanol, (R)-2-amino-3-phenyl-1,1-dibenzylpropanol, 1-((R)-1-amino-2-phenylethyl)cyclobutanol, 1-((R)-1-amino-2-phenylethyl)cyclopentanol, 1-((R)-1-amino-2-phenylethyl)cyclohexanol, and these compounds of which (R) corresponds to (S), and salts thereof such as salts of hydrochloride, salts of sulfuric acid and salts of acetic acid.

The method for producing the above-mentioned optically active aminoalcohol (1) is not particularly limited and for example, those obtained by a known method wherein a starting material is an easily available optically active amino acid or the ester thereof represented by the formula (5) (hereinafter, simply referred to as the optically active amino acid (5)):

(5)

wherein $R^2$ and * are as defined above and $R^6$ represents a C1-4 alkyl group or a hydrogen atom, can be used.

Examples of the C1-4 alkyl groups represented by $R^6$ include a methyl, ethyl, n-propyl, isopropyl, n-butyl and tert-butyl group. Among the optically active amino acid (5), examples of the esters of the optically active amino acids include (R)-alanine methyl ester, (R)-valine methyl ester, (R)-leucine methyl ester, (R)-tert-leucine methyl ester, (R)-phenylglycine methyl ester, (R)-(1-naphthyl)glycine methyl ester, (R)-(2-naphthyl)glycine methyl ester, (R)-phenylalanine methyl ester, and these compounds in which methyl group of the ester moiety is replaced with an ethyl, propyl or n-butyl group; and these compounds of which (R) corresponds to (S). Examples of the amino acids include (R)-alanine, (R)-valine, (R)-leucine, (R)-tert-leucine, (R)-phenylglycine, (R)-(1-naphthyl)glycine, (R)-(2-naphthyl)glycine, (R)-phenylalanine, and these compounds in which (R) corresponds to (S). Further, the optically active amino acid (5) include salts such as a salt of hydrochloride, a salt of sulfuric acid and a salt of acetic acid of the above each compound.

As the method for producing the optically active aminoalcohol (1) wherein the starting material is the optically active amino acid (5), when $R^1$ in the formula (1) is a hydrogen atom, the reaction of the optically active amino acid (5) and a borohydride compound is exemplified (e.g. Tetrahedron Letters, 33, 5517(1992), J. Org. Chem., 58, 3568(1993) and Angew. Chem. Int. Ed. Engl., 28, 218(1989)).

Herein, examples of the borohydride compounds include boron hydride and a complex of it and a compound which can be coordinated to it such as diborane and borane-tetrahydrofuran complex; a mixture comprising a metal borohydride and an acid; a mixture comprising a metal borohydride and a diester of sulfuric acid; and a metal borohydride. When the ester of the optically active amino acid ($R^6$ is a C1-4 alkyl group) is used as the optically active amino acid (5), only the metal borohydride is preferably used as the borohydride compound. When the optically active amino acid ($R^6$ is a hydrogen atom) is used as the optically active amino acid (5), at least one borohydride compound selected from boron hydride and the complex of it and the compound which can be coordinated to it; the mixture comprising the metal borohydride and the acid; the mixture comprising the metal borohydride and the sulfuric acid diester; and the metal borohydride is preferably used as the borohydride compound.

Examples of the metal borohydrides include lithium borohydride, sodium borohydride, potassium borohydride and zinc borohydride, and sodium borohydride is preferably used in terms of availability. Examples of the acids mixed with the metal borohydride include an inorganic acid such as sulfuric acid and hydrochloric acid; and a Lewis acid such as boron trifluoride, zinc chloride, aluminum chloride, titanium tetrachloride, trimethylsilyl chloride and iodine. Examples of the diesters of sulfuric acid include dimethyl sulfate and diethyl sulfate.

As the method for producing the optically active aminoalcohol (1) wherein $R^1$ in the formula (1) is the C1-6 alkyl group, the optionally substituted aralkyl group or the optionally substituted phenyl group, for example, a reaction of the optically active amino acid (5) wherein $R^6$ in the formula (5) is the C1-4 alkyl group and a Grignard reagent is exemplified. Examples of the Grignard reagents include a Grignard reagent represented by the formula (6) (hereinafter, simply referred to as the Grignard reagent (6)):

wherein $R^1$ is as defined above and X represents a halogen atom, and examples of the halogen atoms represented by X include a chlorine atom, a bromine atom and an iodine atom.

Examples of the Grignard reagent (6) include methylmagnesium chloride, ethylmagnesium chloride, n-propylmagnesium chloride, isopropylmagnesium chloride, n-butylmagnesium chloride, isobutylmagnesium chloride, tert-butylmagnesium chloride, n-pentylmagnesium chloride, n-hexylmagnesium chloride, phenylmagnesium chloride, 3-methylphenylmagnesium chloride, 4-methylphenylmagnesium chloride, 2-methoxyphenylmagnesium chloride, 4-methoxyphenylmagnesium chloride, benzylmagnesium chloride, 4-methylbenzylmagnesium chloride, 4-methoxybenzylmagnesium chloride, 1-naphthylmethylmagnesium chloride and 2-naphthylmethylmagnesium chloride, and these compounds in which "chloride" is replaced with "bromide" or "iodide". When $R^1$ represents the C1-6 alkyl group and the compound in which two $R^1$s, which are bonded to the same carbon atom, are bonded to form a ring together with the carbon atom to which they are bonded is desired, the Grignard reagent such as butane-1,4-dimagnesium dichloride, pentane-1,5-dimagnesium dichloride, hexane-1,6-dimagnesium dichloride and these compounds in which "chloride" is replaced with "bromide" or "iodide" may be used as the Grignard reagent.

The configuration of the asymmetric center represented by * in the optically active aminoalcohol (1) obtained is the same as that of the optically active amino acid (5) used.

In the diester compound represented by the formula (2) (hereinafter, simply referred to as the diester (2)), $R^3$ and $R^4$ are the same or different, and each represents a hydrogen atom or a C1-3 alkyl group. $R^5$ represents a C1-3 alkyl group and m represents an integer of 0 to 2 (preferably m=1).

When m is 2 in the diester (2), $R^3$ and $R^4$ preferably represent hydrogen atoms.

Examples of the diester (2) include dimethyl oxalate, diethyl oxalate, dimethyl malonate, diethyl malonate, dimethyl dimethylmalonate, diethyl dimethylmalonate, dimethyl diethylmalonate, diethyl diethylmalonate, dimethyl succinate and diethyl succinate.

The amount of the diester (2) to be used is usually about 0.2 to 2 moles, preferably about 0.4 to 1 mole relative to 1 mole of the optically active aminoalcohol (1).

Examples of the lithium compounds used in the reaction of the optically active aminoalcohol (1) and the diester (2) include lithium hydroxide; a lithium alkoxide such as lithium methoxide and lithium ethoxide; and a lithium halide such as lithium chloride. The amount of them to be used is not particularly limited and it may be catalytic amount. Typically, it is about 0.0005 to 0.5 mole relative to 1 mole of the diester (2).

The reaction is usually carried out in the presence of a solvent. Examples of the solvents to be used include aromatic hydrocarbon solvents such as toluene and xylene; aliphatic hydrocarbon solvents such as hexane, heptane and octane; halogenated hydrocarbon solvents such as chlorobenzene; and ether solvents such as tetrahydrofuran and dimethoxyethane. These solvents may be used alone or by mixing two or more of them. The amount of the solvent to be used is not particularly limited and it is usually about 2 to 500 parts by weight relative to 1 part by weight of the optically active aminoalcohol (1).

The reaction temperature is not particularly limited and it is usually a range of about 20 to 150° C. The reaction is preferably carried out while removing an alcohol produced as a by-product in the reaction represented by the formula (4) (hereinafter, simply referred to as the alcohol (4)):

wherein $R^5$ is as above, out the reaction system at a temperature which is a boiling point of the alcohol (4) and above.

The present reaction is usually carried out under an atmospheric condition and may be carried out under a pressurized condition. It can be also carried out under a reduced pressure in order to remove the alcohol (4) like the above.

The present reaction is carried out by mixing the lithium compound, the optically active aminoalcohol (1), the diester (2) and if necessary in the presence of the solvent, and the mixing order is not particularly limited. For example, it may be carried out by adjusting a reaction temperature after mixing them at a time and by adding the diester (2) to a mixture of the lithium compound and the optically active aminoalcohol (1) whose temperature is adjusted to the reaction temperature.

After completion of the reaction, for example, the optically active bisamidoalcohol compound represented by the formula (3) (hereinafter, simply referred to as the optically active bisamidoalcohol (3)) can be obtained by adding water to the reaction mixture, if necessary conducting extracting treatment using a water-insoluble organic solvent such as toluene and ethyl acetate, and concentrating the organic layer obtained. When the product is precipitated from the reaction mixture, the product can be isolated by the operation such as filtration. The optically active bisamidoalcohol (3) obtained can be further purified by a conventional method such as distillation and recrystallization.

The configuration of the asymmetric center represented by * in the optically active bisamidoalcohol (3) thus obtained is the same as that of the optically active aminoalcohol (1) used.

Examples of the optically active bisamidoalcohol (3) include N,N'-bis[(R)-1-methyl-2-hydroxyethyl]ethane-1,2-diamide, N,N'-bis[(R)-1,2-dimethyl-2-hydroxypropyl]ethane-1,2-diamide, N,N'-bis[(R)-1-methyl-2-ethyl-2-hydroxybutyl]ethane-1,2-diamide, N,N'-bis[(R)-1-methyl-2-n-propyl-2-hydroxypentyl]ethane-1,2-diamide, N,N'-bis[(R)-1-methyl-2,2-diphenyl-2-hydroxyethyl]ethane-1,2-diamide, N,N'-bis[(R)-1-methyl-2,2-di(4-methylphenyl)-2-hydroxyethyl]ethane-1,2-diamide, N,N'-bis[(R)-1-methyl-2,2-di(2-methoxyphenyl)-2-hydroxyethyl]ethane-1,2-diamide, N,N'-bis[(R)-1-methyl-2,2-di(4-methoxyphenyl)-2-hydroxyethyl]ethane-1,2-diamide, N,N'-bis[(R)-1-methyl-2-benzyl-2-hydroxy-3-phenylpropyl]ethane-1,2-diamide, N,N'-bis[(R)-1-(1-hydroxycyclobutyl)ethyl]ethane-1,2-diamide, N,N'-bis[(R)-1-(1-hydroxycyclopentyl)ethyl]ethane-1,2-diamide, N,N'-bis[(R)-1-(1-hydroxycyclohexyl)ethyl]ethane-1,2-diamide, N,N'-bis[(R)-1-isopropyl-2-hydroxyethyl]ethane-1,2-diamide, N,N'-bis[(R)-1-isopropyl-2-methyl-2-hydroxypropyl]ethane-1,2-diamide, N,N'-bis[(R)-1-isopropyl-2-ethyl-2-hydroxybutyl]ethane-1,2-diamide, N,N'-bis[(R)-1-isopropyl-2-n-propyl-2-hydroxypentyl]ethane-1,2-diamide, N,N'-bis[(R)-1-isopropyl-2,2-diphenyl-2-hydroxyethyl]ethane-1,2-diamide, N,N'-bis[(R)-1-isopropyl-2,2-di(4-methylphenyl)-2-hydroxyethyl]ethane-1,2-diamide, N,N'-bis[(R)-1-isopropyl-2,2-di(2-methoxyphenyl)-2-hydroxyethyl]ethane-1,2-diamide, N,N'-bis[(R)-1-isopropyl-2,2-di(4-methoxyphenyl)-2-hydroxyethyl]ethane-1,2-diamide, N,N'-bis[(R)-1-isopropyl-2-benzyl-2-hydroxy-3-phenylpropyl]ethane-1,2-diamide, N,N'-bis[(R)-2-methyl-1-(1-hydroxycyclobutyl)propyl]ethane-1,2-diamide, N,N'-bis[(R)-2-methyl-1-(1-hydroxycyclopentyl)propyl]ethane-1,2-diamide, N,N'-bis[(R)-2-methyl-1-(1-hydroxycyclohexyl)propyl]ethane-1,2-diamide, N,N'-bis[(R)-1-isobutyl-2-hydroxyethyl]ethane-1,2-diamide, N,N'-bis[(R)-1-isobutyl-2-methyl-2-hydroxypropyl]ethane-1,2-diamide, N,N'-bis[(R)-1-isobutyl-2-ethyl-2-hydroxybutyl]ethane-1,2-diamide, N,N'-bis[(R)-1-isobutyl-2-n-propyl-2-hydroxypentyl]ethane-1,2-diamide, N,N'-bis[(R)-1-isobutyl-2,2-diphenyl-2-hydroxyethyl]ethane-1,2-diamide, N,N'-bis[(R)-1-isobutyl-2,2-di(4-methylphenyl)-2-hydroxyethyl]ethane-1,2-diamide, N,N'-bis[(R)-1-isobutyl-2,2-di(2-methoxyphenyl)-2-hydroxyethyl]ethane-1,2-diamide, N,N'-bis[(R)-1-isobutyl-2,2-di(4-methoxyphenyl)-2-hydroxyethyl]ethane-1,2-diamide, N,N'-bis[(R)-1-isobutyl-2-benzyl-2-hydroxy-3-phenylpropyl]ethane-1,2-diamide, N,N'-bis[(R)-3-methyl-1-(1-hydroxycyclobutyl)butyl]ethane-1,2-diamide, N,N'-bis[(R)-3-methyl-1-(1-hydroxycyclopentyl)butyl]ethane-1,2-diamide, N,N'-bis[(R)-3-methyl-1-(1-hydroxycyclohexyl)butyl]ethane-1,2-diamide, N,N'-bis[(R)-1-tert-butyl-2-hydroxyethyl]ethane-1,2-diamide, N,N'-bis[(R)-1-tert-butyl-2-methyl-2-hydroxypropyl]ethane-1,2-diamide, N,N'-bis[(R)-1-tert-butyl-2-ethyl-2-hydroxybutyl]ethane-1,2-diamide, N,N'-bis[(R)-1-tert-butyl-2-n-propyl-2-hydroxypentyl]ethane-1,2-diamide, N,N'-bis[(R)-1-tert-butyl-2,2-diphenyl-2-hydroxyethyl]ethane-1,2-diamide, N,N'-bis[(R)-1-tert-butyl-2,2-di(4-methylphenyl)-2-hydroxyethyl]ethane-1,2-diamide, N,N'-bis[(R)-1-tert-butyl-2,2-di(2-methoxyphenyl)-2-hydroxyethyl]ethane-1,2-diamide, N,N'-bis[(R)-1-tert-butyl-2,2-di(4-methoxyphenyl)-2-hydroxyethyl]ethane-1,2-diamide, N,N'-bis[(R)-1-tert-butyl-2-benzyl-2-hydroxy-3-phenylpropyl]propane-1,3-diamide, N,N'-bis[(R)-2,2-dimethyl-1-(1-hydroxycyclobutyl)propyl]ethane-1,2-diamide, N,N'-bis[(R)-2,2-dimethyl-1-(1-hydroxycyclopentyl)propyl]ethane-1,2-diamide, N,N'-bis[(R)-2,2-dimethyl-1-(1-hydroxycyclohexyl)propyl]ethane-1,2-diamide, N,N'-bis[(R)-1-phenyl-2-hydroxyethyl]ethane-1,2-diamide, N,N'-bis[(R)-1-phenyl-2-methyl-2-hydroxypropyl]ethane-1,2-diamide, N,N'-bis[(R)-1-phenyl-2-ethyl-2-hydroxybutyl]ethane-1,2-diamide, N,N'-bis[(R)-1-phenyl-2-n-propyl-2-hydroxypentyl]ethane-1,2-diamide, N,N'-bis[(R)-1-phenyl-2,2-diphenyl-2-hydroxyethyl]ethane-1,2-diamide, N,N'-bis[(R)-1-phenyl-2,2-di(4-methylphenyl)-2-hydroxyethyl]ethane-1,2-diamide, N,N'-bis[(R)-1-phenyl-2,2-di(2-methoxyphenyl)-2-hydroxyethyl]ethane-1,2-diamide, N,N'-bis[(R)-1-phenyl-2,2-di(4-methoxyphenyl)-2-hydroxyethyl]ethane-1,2-diamide, N,N'-bis[(R)-1-phenyl-2-benzyl-2-hydroxy-3-phenylpropyl]ethane-1,2-diamide, N,N'-bis[(R)-1-phenyl-1-(1-hydroxycyclobutyl)methyl]ethane-1,2-diamide, N,N'-bis[R]-1-phenyl-1-(1-hydroxycyclopentyl)methyl]ethane-1,2-diamide, N,N'-bis[(R)-1-phenyl-1-(1-hydroxycyclohexyl)methyl]ethane-1,2-diamide, N,N'-bis[(R)-1-(1-naphthyl)-2-hydroxyethyl]ethane-1,2-diamide, N,N'-bis[(R)-1-(1-naphthyl)-2-methyl-2-hydroxypropyl]ethane-1,2-diamide, N,N'-bis[(R)-1-(1-naphthyl)-2-ethyl-2-hydroxybutyl]ethane-1,2-diamide, N,N'-bis[(R)-1-(1-naphthyl)-2-n-propyl-2-hydroxypentyl]ethane-1,2-diamide, N,N'-bis[(R)-1-(1-naphthyl)-2,2-diphenyl-2-hydroxyethyl]ethane-1,2-diamide, N,N'-bis[(R)-1-(1-naphthyl)-2,2-di(4-methylphenyl)-2-hydroxyethyl]ethane-1,2-diamide, N,N'-bis[(R)-1-(1-naphthyl)-2,2-di(2-methoxyphenyl)-2-hydroxyethyl]ethane-1,2-diamide, N,N'-bis[(R)-1-(1-naphthyl)-2,2-di(4-methoxyphenyl)-2-hydroxyethyl]ethane-1,2-diamide, N,N'-bis[(R)-1-(1-naphthyl)-2-benzyl-2-hydroxy-3-phenylpropyl]ethane-1,2-diamide, N,N'-bis[(R)-1-(1-naphthyl)-1-(1-hydroxycyclobutyl)methyl]ethane-1,2-diamide, N,N'-bis[R]-1-(1-naphthyl)-1-(1-hydroxycyclopentyl)methyl]ethane-1,2-diamide, N,N'-bis[(R)-1-(1-naphthyl)-1-(1-hydroxycyclohexyl)methyl]ethane-1,2-diamide, N,N'-bis[(R)-1-(2-naphthyl)-2-hydroxyethyl]ethane-1,2-diamide, N,N'-bis[(R)-1-(2-naphthyl)-2-methyl-2-hydroxypropyl]ethane-1,2-diamide, N,N'-bis[(R)-1-(2-naphthyl)-2-ethyl-2-hydroxybutyl]ethane-1,2-diamide, N,N'-bis[(R)-1-(2-naphthyl)-2-n-propyl-2-hydroxypentyl]ethane-1,2-diamide, N,N'-bis[(R)-1-(2-naphthyl)-2,2-diphenyl-2-hydroxyethyl]ethane-1,2-diamide, N,N'-bis[(R)-1-(2-naphthyl)-2,2-di(4-methylphenyl)-2-hydroxyethyl]ethane-1,2-diamide, N,N'-bis[(R)-1-(2-naphthyl)-2,2-di(2-methoxyphenyl)-2-hydroxyethyl]ethane-1,2-diamide, N,N'-bis[(R)-1-(2-naphthyl)-2,2-di(4-methoxyphenyl)-2-hydroxyethyl]ethane-1,2-diamide, N,N'-bis[(R)-1-(2-naphthyl)-2-benzyl-2-hydroxy-3-phenylpropyl]ethane-1,2-diamide, N,N'-bis[(R)-1-(2-naphthyl)-1-(1-hydroxycyclobutyl)methyl]ethane-1,2-diamide, N,N'-bis[R]-1-(2-naphthyl)-1-(1-hydroxycyclopentyl)methyl]ethane-1,2-diamide, N,N'-bis[(R)-1-(2-naphthyl)-1-(1-hydroxycyclohexyl)methyl]ethane-1,2-diamide, N,N'-bis[(R)-1-benzyl-2-hydroxyethyl]ethane-1,2-diamide, N,N'-bis[(R)-1-benzyl-2-methyl-2-hydroxypropyl]ethane-1,2-diamide, N,N'-bis[(R)-1-benzyl-2-ethyl-2-hydroxybutyl]ethane-1,2-diamide, N,N'-bis[(R)-1-benzyl-2-n-propyl-2-hydroxypentyl]ethane-1,2-diamide, N,N'-bis[(R)-1-benzyl-2,2-diphenyl-2-hydroxyethyl]ethane-1,2-diamide, N,N'-bis[(R)-1-benzyl-2,2-di(4-methylphenyl)-2-hydroxyethyl]ethane-1,2-diamide, N,N'-bis[(R)-1-benzyl-2,2-di(2-methoxyphenyl)-2-hydroxyethyl]ethane-1,2-diamide, N,N'-bis[(R)-1-benzyl-2,2-di(4-methoxyphenyl)-2-hydroxyethyl]ethane-1,2-diamide, N,N'-bis[(R)-1-benzyl-2-benzyl-2-hydroxy-3-phenylpropyl]ethane-1,2-diamide, N,N'-bis[(R)-2-phenyl-1-(1-hydroxycyclobutyl)ethyl]ethane-1,2-diamide, N,N'-bis[(R)-2-phenyl-1-(1-hydroxycyclopentyl)ethyl]ethane-1,2-diamide, N,N'-bis[(R)-2-phenyl-1-(1-hydroxycyclohexyl)ethyl]ethane-1,2-diamide, N,N'-bis[(R)-1-methyl-2-hydroxyethyl]propane-1,3-diamide, N,N'-bis[(R)-1,2-dimethyl-2-hydroxypropyl]propane-1,3-diamide, N,N'-bis[(R)-1-methyl-2-ethyl-2-hydroxybutyl]propane-1,3-diamide, N,N'-bis[(R)-1-methyl-2-n-propyl-2-hydroxypentyl]propane-1,3-diamide, N,N'-bis[(R)-1-methyl-2,2-diphenyl-2-hydroxyethyl]propane-1,3-diamide, N,N'-bis[(R)-1-methyl-2,2-di(4-methylphenyl)-2-hydroxyethyl]propane-1,3-diamide, N,N'-bis[(R)-1-methyl-2,2-di(2-methoxyphenyl)-2-hydroxyethyl]propane-1,3-diamide, N,N'-bis[(R)-1-methyl-2,2-di(4-methoxyphenyl)-2hydroxyethyl]propane-1,3-diamide, N,N'-bis[(R)-1-methyl-2-benzyl-2-hydroxy-3-phenylpropyl]propane-1,3-diamide, N,N'-bis[(R)-1-(1-hydroxycyclobutyl)ethyl]propane-1,3-diamide, N,N'-bis[(R)-1-(1-hydroxycyclopentyl)ethyl]propane-1,3-diamide, N,N'-bis[(R)-1-(1-hydroxycyclohexyl)ethyl]propane-1,3-diamide, N,N'-bis[(R)-1-isopropyl-2-hydroxyethyl]propane-1,3-diamide, N,N'-bis[(R)-1-isopropyl-2-methyl-2-hydroxypropyl]propane-1,3-diamide, N,N'-bis[(R)-1-isopropyl-2-ethyl-2-hydroxybutyl]propane-1,3-diamide, N,N'-bis[(R)-1-isopropyl-2-n-propyl-2-hydroxypentyl]propane-1,3-diamide, N,N'-bis[(R)-1-isopropyl-2,2-diphenyl-2-hydroxyethyl]propane-1,3-diamide, N,N'-bis[(R)-1-isopropyl-2,2-di(4-methylphenyl)-2-hydroxyethyl]propane-1,3-diamide, N,N'-bis[(R)-1-isopropyl-2,2-di(2-methoxyphenyl)-2-hydroxyethyl]propane-1,3-diamide, N,N'-bis[(R)-1-isopropyl-2,2-di(4-methoxyphenyl)-2-hydroxyethyl]propane-1,3-diamide, N,N'-bis[(R)-1-isopropyl-2-benzyl-2-hydroxy-3-phenylpropyl]propane-1,3-diamide, N,N'-bis[(R)-2-methyl-1-(1-hydroxycyclobutyl)propyl]propane-1,3-diamide, N,N'-bis[(R)-2-methyl-1-(1-hydroxycyclopentyl)propyl]propane-1,3-diamide, N,N'-bis[(R)-2-methyl-1-(1-hydroxycyclohexyl)propyl]propane-1,3-diamide, N,N'-bis[(R)-1-isobutyl-2-hydroxyethyl]propane-1,3-diamide, N,N'-bis[(R)-1-isobutyl-2-methyl-2-hydroxypropyl]propane-1,3-diamide, N,N'-bis[(R)-1-isobutyl-2-ethyl-2-hydroxybutyl]propane-1,3-diamide, N,N'-bis[(R)-1-isobutyl-2-n-propyl-2-hydroxypentyl]propane-1,3-diamide, N,N'-bis[(R)-1-isobutyl-2,2-diphenyl-2-hydroxyethyl]propane-1,3-diamide, N,N'-bis[(R)-1-isobutyl-2,2-di(4-methylphenyl)-2-hydroxyethyl]propane-1,3-diamide, N,N'-bis[(R)-1-isobutyl-2,2-di(2-methoxyphenyl)-2-hydroxyethyl]propane-1,3-diamide, N,N'-bis[(R)-1-isobutyl-2,2-di(4-methoxyphenyl)-2-hydroxyethyl]propane-1,3-diamide, N,N'-bis[(R)-1-isobutyl-2-benzyl-2-hydroxy-3-phenylpropyl]propane-1,3-diamide, N,N'-bis[(R)-3-methyl-1-(1-hydroxycyclobutyl)butyl]propane-1,3-diamide, N,N'-bis[(R)-3-methyl-1-(1-hydroxycyclopentyl)butyl]propane-1,3-diamide, N,N'-bis[(R)-3-methyl-1-(1-hydroxycyclohexyl)butyl]propane-1,3-diamide, N,N'-bis[(R)-1-tert-butyl-2-hydroxyethyl]propane-1,3-diamide, N,N'-bis[(R)-1-tert-butyl-2-methyl-2-hydroxypropyl]propane-1,3-diamide, N,N'-bis[(R)-1-tert-butyl-2-ethyl-2-hydroxybutyl]propane-1,3-diamide, N,N'-bis[(R)-1-tert-butyl-2-n-propyl-2-hydroxypentyl]propane-1,3-diamide, N,N'-bis[(R)-1-tert-butyl-2,2-diphenyl-2-hydroxyethyl]propane-1,3-diamide, N,N'-bis[(R)-1-tert-butyl-2,2-di(4-methylphenyl)-2-hydroxyethyl]propane-1,3-diamide, N,N'-bis[(R)-1-tert-butyl-2,2-di(2-methoxyphenyl)-2-hydroxyethyl]propane-1,3-diamide, N,N'-bis[(R)-1-tert-butyl-2,2-di(4-methoxyphenyl)-2-hydroxyethyl]propane-1,3-diamide, N,N'-bis[(R)-1-tert-butyl-2-benzyl-2-hydroxy-3-phenylpropyl]propane-1,3-diamide, N,N'-bis[(R)-2,2-dimethyl-1-(1-hydroxycyclobutyl)propyl]propane-1,3-diamide, N,N'-bis[(R)-2,2-dimethyl-1-(1-hydroxycyclopentyl)propyl]propane-1,3-diamide, N,N'-bis[(R)-2,2-dimethyl-1-(1-hydroxycyclohexyl)propyl]propane-1,3-diamide, N,N'-bis[(R)-1-phenyl-2-hydroxyethyl]propane-1,3-diamide, N,N'-bis[(R)-1-phenyl-2-methyl-2-hydroxypropyl]propane-1,3-diamide, N,N'-bis[(R)-1-phenyl-2-ethyl-2-hydroxybutyl]propane-1,3-diamide, N,N'-bis[(R)-1-phenyl-2-n-propyl-2-hydroxypentyl]propane-1,3-diamide, N,N'-bis[(R)-1-phenyl-2,2-diphenyl-2-hydroxyethyl]propane-1,3-diamide, N,N'-bis[(R)-1-phenyl-2,2-di(4-methylphenyl)-2-hydroxyethyl]propane-1,3-diamide, N,N'-bis[(R)-1-phenyl-2,2-di(2-methoxyphenyl)-2-hydroxyethyl]propane-1,3-diamide, N,N'-bis[(R)-1-phenyl-2,2-di(4-methoxyphenyl)-2-hydroxyethyl]propane-1,3-diamide, N,N'-bis[(R)-1-phenyl-2-benzyl-2-hydroxy-3-phenylpropyl]propane-1,3-diamide, N,N'-bis[(R)-1-phenyl-1-(1-hydroxycyclobutyl)methyl]propane-1,3-diamide, N,N'-bis[R]-1-phenyl-1-(1-hydroxycyclopentyl)methyl]propane-1,3-diamide, N,N'-bis[(R)-1-phenyl-1-(1-hydroxycyclohexyl)methyl]propane-1,3-diamide, N,N'-bis[(R)-1-(1-naphthyl)-2-hydroxyethyl]propane-1,3-diamide, N,N'-bis[(R)-1-(1-naphthyl)-2-methyl-2-hydroxypropyl]propane-1,3-diamide, N,N'-bis[(R)-1-(1-naphthyl)-2-ethyl-2-hydroxybutyl]propane-1,3-diamide, N,N'-bis[(R)-1-(1-naphthyl)-2-n-propyl-2-hydroxypentyl]propane-1,3-diamide, N,N'-bis[(R)-1-(1-naphthyl)-2,2-diphenyl-2-hydroxyethyl]propane-1,3-diamide, N,N'-bis[(R)-1-(1-naphthyl)-2,2-di(4-methylphenyl)-2-hydroxyethyl]propane-1,3-diamide, N,N'-bis[(R)-1-(1-naphthyl)-2,2-di(2-methoxyphenyl)-2-hydroxyethyl]propane-1,3-diamide, N,N'-bis[(R)-1-(1-naphthyl)-2,2-di(4-methoxyphenyl)-2-hydroxyethyl]propane-1,3-diamide, N,N'-bis[(R)-1-(1-naphthyl)-2-benzyl-2-hydroxy-3-phenylpropyl]propane-1,3-diamide, N,N'-bis[(R)-1-(1-naphthyl)-1-(1-hydroxycyclobutyl)methyl]propane-1,3-diamide, N,N'-bis[R]-1-(1-naphthyl)-1-(1-hydroxycyclopentyl)methyl]propane-1,3-diamide, N,N'-bis[(R)-1-(1-naphthyl)-1-(1-hydroxycyclohexyl)methyl]propane-1,3-diamide, N,N'-bis[(R)-1-(2-naphthyl)-2-hydroxyethyl]propane-1,3-diamide, N,N'-bis[(R)-1-(2-naphthyl)-2-methyl-2-hydroxypropyl]propane-1,3-diamide, N,N'-bis[(R)-1-(2-naphthyl)-2-ethyl-2-hydroxybutyl]propane-1,3-diamide, N,N'-bis[(R)-1-(2-naphthyl)-2-n-propyl-2-hydroxypentyl]propane-1,3-diamide, N,N'-bis[(R)-1-(2-naphthyl)-2,2-diphenyl-2-hydroxyethyl]propane-1,3-diamide, N,N'-bis[(R)-1-(2-naphthyl)-2,2-di(4-methylphenyl)-2-hydroxyethyl]propane-1,3-diamide, N,N'-bis[(R)-1-(2-naphthyl)-2,2-di(2-methoxyphenyl)-2-hydroxyethyl]propane-1,3-diamide, N,N'-bis[(R)-1-(2-naphthyl)-2,2-di(4-methoxyphenyl)-2-hydroxyethyl]propane-1,3-diamide, N,N'-bis[(R)-1-(2-naphthyl)-2-benzyl-2-hydroxy-3-phenylpropyl]propane-1,3-diamide, N,N'-bis[(R)-1-(2-naphthyl)-1-(1-hydroxycyclobutyl)methyl]propane-1,3-diamide, N,N'-bis[R]-1-(2-naphthyl)-1-(1-hydroxycyclopentyl)methyl]propane-1,3-diamide, N,N'-bis[(R)-1-(2-naphthyl)-1-(1-hydroxycyclohexyl)methyl]propane-1,3-diamide, N,N'-bis[(R)-1-benzyl-2-hydroxyethyl]propane-1,3-diamide, N,N'-bis[(R)-1-benzyl-2-methyl-2-hydroxypropyl]propane-1,3-diamide, N,N'-bis[(R)-1-benzyl-2-ethyl-2-hydroxybutyl]propane-1,3-diamide, N,N'-bis[(R)-1-benzyl-2-n-propyl-2-hydroxypentyl]propane-1,3-diamide, N,N'-bis

[(R)-1-benzyl-2,2-diphenyl-2-hydroxyethyl]propane-1,3-diamide, N,N'-bis[(R)-1-benzyl-2,2-di(4-methylphenyl)-2-hydroxyethyl]propane-1,3-diamide, N,N'-bis[(R)-1-benzyl-2,2-di(2-methoxyphenyl)-2-hydroxyethyl]propane-1,3-diamide, N,N'-bis[(R)-1-benzyl-2,2-di(4-methoxyphenyl)-2-hydroxyethyl]propane-1,3-diamide, N,N'-bis[(R)-1-benzyl-2-benzyl-2-hydroxy-3-phenylpropyl]propane-1,3-diamide, N,N'-bis[(R)-2-phenyl-1-(1-hydroxycyclobutyl)ethyl]propane-1,3-diamide, N,N'-bis[(R)-2-phenyl-1-(1-hydroxycyclopentyl)ethyl]propane-1,3-diamide, N,N'-bis[(R)-2-phenyl-1-(1-hydroxycyclohexyl)ethyl]propane-1,3-diamide, N,N'-bis[(R)-1-methyl-2-hydroxyethyl]-2,2-dimethylpropane-1,3-diamide, N,N'-bis[(R)-1,2-dimethyl-2-hydroxypropyl]-2,2-dimethylpropane-1,3-diamide, N,N'-bis[(R)-1-methyl-2-ethyl-2-hydroxybutyl]-2,2-dimethylpropane-1,3-diamide, N,N'-bis[(R)-1-methyl-2-n-propyl-2-hydroxypentyl]-2,2-dimethylpropane-1,3-diamide, N,N'-bis[(R)-1-methyl-2,2-diphenyl-2-hydroxyethyl]-2,2-dimethylpropane-1,3-diamide, N,N'-bis[(R)-1-methyl-2,2-di(4-methylphenyl)-2-hydroxyethyl]-2,2-dimethylpropane-1,3-diamide, N,N'-bis[(R)-1-methyl-2,2-di(2-methoxyphenyl)-2-hydroxyethyl]-2,2-dimethylpropane-1,3-diamide, N,N'-bis[(R)-1-methyl-2,2-di(4-methoxyphenyl)-2-hydroxyethyl]-2,2-dimethylpropane-1,3-diamide, N,N'-bis[(R)-1-methyl-2-benzyl-2-hydroxy-3-phenylpropyl]-2,2-dimethylpropane-1,3-diamide, N,N'-bis[(R)-1-(1-hydroxycyclobutyl)ethyl]-2,2-dimethylpropane-1,3-diamide, N,N'-bis[(R)-1-(1-hydroxycyclopentyl)ethyl]-2,2-dimethylpropane-1,3-diamide, N,N'-bis[(R)-1-(1-hydroxycyclohexyl)ethyl]-2,2-dimethylpropane-1,3-diamide, N,N'-bis[(R)-1-isopropyl-2-hydroxyethyl]-2,2-dimethylpropane-1,3-diamide, N,N'-bis[(R)-1-isopropyl-2-methyl-2-hydroxypropyl]-2,2-dimethylpropane-1,3-diamide, N,N'-bis[(R)-1-isopropyl-2-ethyl-2-hydroxybutyl]-2,2-dimethylpropane-1,3-diamide, N,N'-bis[(R)-1-isopropyl-2-n-propyl-2-hydroxypentyl]-2,2-dimethylpropane-1,3-diamide, N,N'-bis[(R)-1-isopropyl-2,2-diphenyl-2-hydroxyethyl]-2,2-dimethylpropane-1,3-diamide, N,N'-bis[(R)-1-isopropyl-2,2-di(4-methylphenyl)-2-hydroxyethyl]-2,2-dimethylpropane-1,3-diamide, N,N'-bis[(R)-1-isopropyl-2,2-di(2-methoxyphenyl)-2-hydroxyethyl]-2,2-dimethylpropane-1,3-diamide, N,N'-bis[(R)-1-isopropyl-2,2-di(4-methoxyphenyl)-2-hydroxyethyl]-2,2-dimethylpropane-1,3-diamide, N,N'-bis[(R)-1-isopropyl-2-benzyl-2-hydroxy-3-phenylpropyl]-2,2-dimethylpropane-1,3-diamide, N,N'-bis[(R)-2-methyl-1-(1-hydroxycyclobutyl)propyl]-2,2-dimethylpropane-1,3-diamide, N,N'-bis[(R)-2-methyl-1-(1-hydroxycyclopentyl)propyl]-2,2-dimethylpropane-1,3-diamide, N,N'-bis[(R)-2-methyl-1-(1-hydroxycyclohexyl)propyl]-2,2-dimethylpropane-1,3-diamide, N,N'-bis[(R)-1-isobutyl-2-hydroxyethyl]-2,2-dimethylpropane-1,3-diamide, N,N'-bis[(R)-1-isobutyl-2-methyl-2-hydroxypropyl]-2,2-dimethylpropane-1,3-diamide, N,N'-bis[(R)-1-isobutyl-2-ethyl-2-hydroxybutyl]-2,2-dimethylpropane-1,3-diamide, N,N'-bis[(R)-1-isobutyl-2-n-propyl-2-hydroxypentyl]-2,2-dimethylpropane-1,3-diamide, N,N'-bis[(R)-1-isobutyl-2,2-diphenyl-2-hydroxyethyl]-2,2-dimethylpropane-1,3-diamide, N,N'-bis[(R)-1-isobutyl-2,2-di(4-methylphenyl)-2-hydroxyethyl]-2,2-dimethylpropane-1,3-diamide, N,N'-bis[(R)-1-isobutyl-2,2-di(2-methoxyphenyl)-2-hydroxyethyl]-2,2-dimethylpropane-1,3-diamide, N,N'-bis[(R)-1-isobutyl-2,2-di(4-methoxyphenyl)-2-hydroxyethyl]-2,2-dimethylpropane-1,3-diamide, N,N'-bis[(R)-1-isobutyl-2-benzyl-2-hydroxy-3-phenylpropyl]-2,2-dimethylpropane-1,3-diamide, N,N'-bis[(R)-3-methyl-1-(1-hydroxycyclobutyl)butyl]-2,2-dimethylpropane-1,3-diamide, N,N'-bis[(R)-3-methyl-1-(1-hydroxycyclopentyl)butyl]-2,2-dimethylpropane-1,3-diamide, N,N'-bis[(R)-3-methyl-1-(1-hydroxycyclohexyl)butyl]-2,2-dimethylpropane-1,3-diamide, N,N'-bis[(R)-1-tert-butyl-2-hydroxyethyl]-2,2-dimethylpropane-1,3-diamide, N,N'-bis[(R)-1-tert-butyl-2-methyl-2-hydroxypropyl]-2,2-dimethylpropane-1,3-diamide, N,N'-bis[(R)-1-tert-butyl-2-ethyl-2-hydroxybutyl]-2,2-dimethylpropane-1,3-diamide, N,N'-bis[(R)-1-tert-butyl-2-n-propyl-2-hydroxypentyl]-2,2-dimethylpropane-1,3-diamide, N,N'-bis[(R)-1-tert-butyl-2,2-diphenyl-2-hydroxyethyl]-2,2-dimethylpropane-1,3-diamide, N,N'-bis[(R)-1-tert-butyl-2,2-di(4-methylphenyl)-2-hydroxyethyl]-2,2-dimethylpropane-1,3-diamide, N,N'-bis[(R)-1-tert-butyl-2,2-di(2-methoxyphenyl)-2-hydroxyethyl]-2,2-dimethylpropane-1,3-diamide, N,N'-bis[(R)-1-tert-butyl-2,2-di(4-methoxyphenyl)-2-hydroxyethyl]-2,2-dimethylpropane-1,3-diamide, N,N'-bis[(R)-1-tert-butyl-2-benzyl-2-hydroxy-3-phenylpropyl]-2,2-dimethylpropane-1,3-diamide, N,N'-bis[(R)-2,2-dimethyl-1-(1-hydroxycyclobutyl)propyl]-2,2-dimethylpropane-1,3-diamide, N,N'-bis[(R)-2,2-dimethyl-1-(1-hydroxycyclopentyl)propyl]-2,2-dimethylpropane-1,3-diamide, N,N'-bis[(R)-2,2-dimethyl-1-(1-hydroxycyclohexyl)propyl]-2,2-dimethylpropane-1,3-diamide, N,N'-bis[(R)-1-phenyl-2-hydroxyethyl]-2,2-dimethylpropane-1,3-diamide, N,N'-bis[(R)-1-phenyl-2-methyl-2-hydroxypropyl]-2,2-dimethylpropane-1,3-diamide, N,N'-bis[(R)-1-phenyl-2-ethyl-2-hydroxybutyl]-2,2-dimethylpropane-1,3-diamide, N,N'-bis[(R)-1-phenyl-2-n-propyl-2-hydroxypentyl]-2,2-dimethylpropane-1,3-diamide, N,N'-bis[(R)-1-phenyl-2,2-diphenyl-2-hydroxyethyl]-2,2-dimethylpropane-1,3-diamide, N,N'-bis[(R)-1-phenyl-2,2-di(4-methylphenyl)-2-hydroxyethyl]-2,2-dimethylpropane-1,3-diamide, N,N'-bis[(R)-1-phenyl-2,2-di(2-methoxyphenyl)-2-hydroxyethyl]-2,2-dimethylpropane-1,3-diamide, N,N'-bis[(R)-1-phenyl-2,2-di(4-methoxyphenyl)-2-hydroxyethyl]-2,2-dimethylpropane-1,3-diamide, N,N'-bis[(R)-1-phenyl-2-benzyl-2-hydroxy-3-phenylpropyl]-2,2-dimethylpropane-1,3-diamide, N,N'-bis[(R)-1-phenyl-1-(1-hydroxycyclobutyl)methyl]-2,2-dimethylpropane-1,3-diamide, N,N'-bis[R]-1-phenyl-1-(1-hydroxycyclopentyl)methyl]-2,2-dimethylpropane-1,3-diamide, N,N'-bis[(R)-1-phenyl-1-(1-hydroxycyclohexyl)methyl]-2,2-dimethylpropane-1,3-diamide, N,N'-bis[(R)-1-(1-naphthyl)-2-hydroxyethyl]-2,2-dimethylpropane-1,3-diamide, N,N'-bis[(R)-1-(1-naphthyl)-2-methyl-2-hydroxypropyl]-2,2-dimethylpropane-1,3-diamide, N,N'-bis[(R)-1-(1-naphthyl)-2-ethyl-2-hydroxybutyl]-2,2-dimethylpropane-1,3-diamide, N,N'-bis[(R)-1-(1-naphthyl)-2-n-propyl-2-hydroxypentyl]-2,2-dimethylpropane-1,3-diamide, N,N'-bis[(R)-1-(1-naphthyl)-2,2-diphenyl-2-hydroxyethyl]-2,2-dimethylpropane-1,3-diamide, N,N'-bis[(R)-1-(1-naphthyl)-2,2-di(4-methylphenyl)-2-hydroxyethyl]-2,2-dimethylpropane-1,3-diamide, N,N'-bis[(R)-1-(1-naphthyl)-2,2-di(2-methoxyphenyl)-2-hydroxyethyl]-2,2-dimethylpropane-1,3-diamide, N,N'-bis[(R)-1-(1-naphthyl)-2,2-di(4-methoxyphenyl)-2-hydroxyethyl]-2,2-dimethylpropane-1,3-diamide, N,N'-bis[(R)-1-(1-naphthyl)-2-benzyl-2-hydroxy-3-phenylpropyl]-2,2-dimethylpropane-1,3-diamide, N,N'-bis[(R)-1-(1-naphthyl)-1-(1-hydroxycyclobutyl)methyl]-2,2-dimethylpropane-1,3-diamide, N,N'-bis[R]-1-(1-naphthyl)-1-(1-hydroxycyclopentyl)methyl]-2,2- dimethylpropane-1,3-diamide, N,N'-bis[(R)-1-(1-naphthyl)-1-(1-hydroxycyclohexyl)methyl]-2,2-dimethylpropane-1,3-diamide, N,N'-bis[(R)-1-(2-naphthyl)-2-hydroxyethyl]-2,2-dimethylpropane-1,3-diamide, N,N'-bis[(R)-1-(2-naphthyl)-2-methyl-2-hydroxypropyl]-2,2-dimethylpropane-1,3-diamide, N,N'-bis[(R)-1-(2-naphthyl)-2-ethyl-2-hydroxybutyl]-2,2-dimethylpropane-1,3-diamide, N,N'-bis[(R)-1-(2-naphthyl)-2-n-propyl-2-hydroxypentyl]-2,2-dimethylpropane-1,3-diamide, N,N'-bis[(R)-1-(2-naphthyl)-2,2-diphenyl-2-hydroxyethyl]-2,2-dimethylpropane-1,3-diamide, N,N'-bis[(R)-1-(2-naphthyl)-2,2-di(4-methylphenyl)-2-hydroxyethyl]-2,2-dimethylpropane-1,3-diamide, N,N'-bis[(R)-1-(2-naphthyl)-2,2-di(2-methoxyphenyl)-2-hydroxyethyl]-2,2-dimethylpropane-1,3-diamide, N,N'-bis[(R)-1-(2-naphthyl)-2,2-di(4-methoxyphenyl)-2-hydroxyethyl]-2,2-dimethylpropane-1,3-diamide, N,N'-bis[(R)-1-(2-naphthyl)-2-benzyl-2-hydroxy-3-phenylpropyl]-2,2-dimethylpropane-1,3-hydroxycyclobutyl)methyl]-2,2-dimethylpropane-1,3-diamide, -diamide, N,N'-bis[(R)-1-(2-naphthyl)-1-(1N,N'-bis[R]-1-(2-naphthyl)-1-(1-hydroxycyclopentyl)methyl]-2,2-dimethylpropane-1,3-diamide, N,N'-bis[(R)-1-(2-naphthyl)-1-(1-hydroxycyclohexyl)methyl]-2,2-dimethylpropane-1,3-diamide, N,N'-bis[(R)-1-benzyl-2-hydroxyethyl]-2,2-dimethylpropane-1,3-diamide, N,N'-bis[(R)-1-benzyl-2-methyl-2-hydroxypropyl]-2,2-dimethylpropane-1,3-diamide, N,N'-bis[(R)-1-benzyl-2-ethyl-2-hydroxybutyl]-2,2-dimethylpropane-1,3-diamide, N,N'-bis[(R)-1-benzyl-2-n-propyl-2-hydroxypentyl]-2,2-dimethylpropane-1,3-diamide, N,N'-bis[(R)-1-benzyl-2,2-diphenyl-2-hydroxyethyl]-2,2-dimethylpropane-1,3-diamide, N,N'-bis[(R)-1-benzyl-2,2-di(4-methylphenyl)-2-hydroxyethyl]-2,2-dimethylpropane-1,3-diamide, N,N'-bis[(R)-1-benzyl-2,2-di(2-methoxyphenyl)-2-hydroxyethyl]-2,2-dimethylpropane-1,3-diamide, N,N'-bis[(R)-1-benzyl-2,2-di(4-methoxyphenyl)-2-hydroxyethyl]-2,2-dimethylpropane-1,3-diamide, N,N'-bis[(R)-1-benzyl-2-benzyl-2-hydroxy-3-phenylpropyl]-2,2-dimethylpropane-1,3-diamide, N,N'-bis[(R)-2-phenyl-1-(1-hydroxycyclobutyl)ethyl]-2,2-dimethylpropane-1,3-diamide, N,N'-bis[(R)-2-phenyl-1-(1-hydroxycyclopentyl)ethyl]-2,2-dimethylpropane-1,3-diamide, N,N'-bis[(R)-2-phenyl-1-(1-hydroxycyclohexyl)ethyl]-2,2-dimethylpropane-1,3-diamide; and these compounds of which the configuration (R) is changed to (S). The optically active bisamidoalcohol compound obtained can be converted into a corresponding optically active bisoxazoline compound represented by the following formula (7):

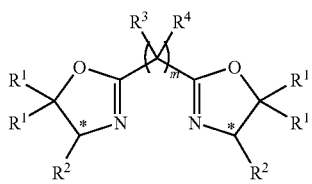

(7)

wherein $R^1$, $R^2$, $R^3$, $R^4$ and m are as defined for the above-mentioned formula (2) or (3), or as illustrated as the preferable embodiment thereof, by conducting a cyclodehydration reaction according to a method described in U.S. Pat. No. 6,410,741.

EXAMPLES

The present invention will be further illustrated in more detail by Examples. The present invention is not limited to these Examples.

Example 1

In a 100 mL Schlenk tube purged with nitrogen, 980 mg (7.14 mmol) of (R)-phenylglycinol, 472 mg (3.57 mmol) of dimethyl malonate, 6.8 mg (0.18 mmol) of lithium methoxide and 40 mL of normal heptane were mixed and the resulting mixture was stirred at 100° C. for 3 hours. The homogeneous solution became a white suspension as the reaction progresses. After that, reaction solution was cooled to room temperature and filtered. The obtained powder was dried to obtain 1.15 g of a white powder of N,N'-bis[(R)-1-phenyl-2-hydroxyethyl]propane-1,3-diamide.

Yield: 94% (based on dimethyl malonate).

Example 2

According to the same manner as that described in Example 1, 1.20 g of a white powder of N,N'-bis[(S)-1-tert-butyl-2-hydroxyethyl]propane-1,3-diamide was obtained except that 980 mg (8.36 mmol) of (S)-tert-leucinol, 552 mg (4.18 mmol) of dimethyl malonate and 7.9 mg (0.21 mmol) of lithium methoxide were used as each reaction agent.

Yield: 95% (based on dimethyl malonate).

Example 3

According to the same manner as that described in Example 1, 1.79 g of a white powder of N,N'-bis[(S)-1-tert-butyl-2-hydroxyethyl]ethane-1,2-diamide was obtained except that 1.470 g (12.5 mmol) of (S)-tert-leucinol, 741 mg (6.27 mmol) of dimethyl oxalate and 11.9 mg (0.31 mmol) of lithium methoxide were used as each reaction agent.

Yield: 99% (based on dimethyl oxalate).

Example 4-1

Synthesis of (S)-tert-leucinol

To a 100 mL Schlenk tube purged with nitrogen, 4.00 g (30.5 mmol) of (S)-tert-leucine and 20 mL of tetrahydrofuran were added and the inner temperature was adjusted to 10° C. To this suspension, 61.0 mL (61.0 mmol) of 1M borane-tetrahydrofuran complex was added dropwise over 30 minutes and the resulting mixture was stirred at the same temperature for 1 hour. After that, The mixture was heated to an inner temperature of 65° C. and stirred at the same temperature for 4 hours. After the reaction mixture was cooled to 10° C., 8 mL of methanol was added dropwise thereto over 20 minutes. After reaction mixture was concentrated using an evaporator, 20 mL of 4M aqueous sodium hydroxide solution was added thereto and stirred at room temperature for 1 hour. Next, the extraction was conducted by adding 40 mL of tert-butyl methyl ether and the organic layer obtained was dehydrated over sodium sulfate. Sodium sulfate was removed by filtration and tert-butyl methyl ether was distilled away by atmospheric distillation. Further, 2.82 g of (S)-tert-leucinol was obtained as a fraction of 70 to 75° C. by reduced-pressure distillation (0.3 kPa).

Yield: 79%.

Example 4-2

Synthesis of N,N'-bis[(S)-1-tert-butyl-2-hydroxyethyl]propane-1,3-diamide

According to the same manner as that described in Example 2, 2.99 g of a white powder of N,N'-bis[(S)-1-tert-butyl-2-hydroxyethyl]propane-1,3-diamide was obtained except that 2.42 g (20.7 mmol) of (S)-tert-leucinol obtained in Example 4-1, 1.36 g (10.3 mmol) of dimethyl malonate and 19.6 mg (0.52 mmol) of lithium methoxide were used.

Yield: 96% (based on dimethyl malonate).

INDUSTRIAL APPLICABILITY

According to the present invention, an optically active bisamidoalcohol compound, which is useful as an intermediate of a ligand of an asymmetric synthesis catalyst, can be efficiently and inexpensively produced. Therefore, it is industrially advantageous.

The invention claimed is:

1. A method for producing an optically active bisamidoalcohol compound represented by the formula (3):

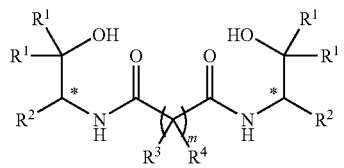

(3)

wherein $R^1$ represents a C1-6 alkyl group, an optionally substituted phenyl group, an optionally substituted aralkyl group or a hydrogen atom, or two $R^1$s, which are bonded to the same carbon atom, are bonded to form a ring together with the carbon atom to which they are bonded, $R^2$ represents a C1-6 alkyl group, an optionally substituted phenyl group, a 1-naphthyl group, a 2-naphthyl group or an optionally substituted aralkyl group, $R^3$ and $R^4$ are the same or different, and each represents a hydrogen atom or C1-3 alkyl group, m represents an integer of 0 to 2, and

* represents an asymmetric center, which comprises reacting an optically active aminoalcohol compound represented by the formula (1):

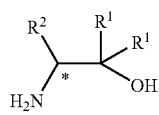

(1)

wherein $R^1$, $R^2$ and * are as defined above,
with a diester compound represented by the formula (2):

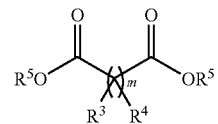

(2)

wherein $R^3$, $R^4$ and m are as defined above and $R^5$ represents a C1-3 alkyl group, in the presence of a lithium compound, wherein the lithium compound is at least one lithium compound selected from lithium hydroxide, a lithium alkoxide and a lithium halide.

2. The method according to claim 1, wherein $R^1$ represents a C1-6 alkyl group,
 a phenyl group which may be substituted with at least one selected from a C1-6 alkyl group and a C1-6 alkoxy group,
 a C7-16 aralkyl group which may be substituted with at least one substituent selected from a C1-6 alkyl group and a C1-6 alkoxy group, or a hydrogen atom, or
 two $R^1$s, which are bonded to the same carbon atom, are bonded to form a C3-6 cycloalkane together with the carbon atom to which they are bonded, and $R^2$ represents a C1-6 alkyl group,
 a phenyl group which may be substituted with at least one selected from a C1-6 alkyl group and a C1-6 alkoxy group, or
 a C7-16 aralkyl group which may be substituted with at least one substituent selected from a C1-6 alkyl group and a C1-6 alkoxy group.

3. The method according to claim 1 or 2, wherein $R^2$ a phenyl, 3-methylphenyl, 4-methylphenyl, 2-methoxyphenyl or 4-methoxyphenyl group.

4. The method according to claim 1, wherein the lithium alkoxide is lithium methoxide or lithium ethoxide.

5. The method according to claim 1, wherein the lithium halide is lithium chloride.

6. The method according to claim 1, wherein the reaction is carried out while removing an alcohol produced as a by-product represented by the formula (4):

$R^5OH$ (4)

wherein $R^5$ represents a C1-4 alkyl group.

7. The method according to claim 1, wherein the optically active aminoalcohol compound of the formula (1) is the optically active aminoalcohol compound obtained by reacting an optically active amino acid or the ester thereof represented by the formula (5):

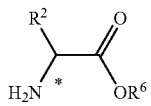

(5)

wherein $R^2$ and * are as defined above and $R^6$ represents a C1-4 alkyl group or a hydrogen atom, with a borohydride compound.

* * * * *